US012582924B2

(12) United States Patent
Chua

(10) Patent No.: US 12,582,924 B2
(45) Date of Patent: Mar. 24, 2026

(54) METHODS FOR OBTAINING LIQUID FROM A SOLID PHASE

(71) Applicant: Cambridge Enterprise Limited, Cambridge (GB)

(72) Inventor: Yii Leng Chua, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 41 days.

(21) Appl. No.: 15/789,410

(22) Filed: Oct. 20, 2017

(65) Prior Publication Data

US 2018/0257002 A1    Sep. 13, 2018

Related U.S. Application Data

(62) Division of application No. 13/834,901, filed on Mar. 15, 2013, now Pat. No. 9,821,248.

(30) Foreign Application Priority Data

Mar. 16, 2012    (GB) ..................................... 1204663

(51) Int. Cl.

| | |
|---|---|
| *B01D 15/20* | (2006.01) |
| *B01D 11/02* | (2006.01) |
| *B01D 15/00* | (2006.01) |
| *B01D 15/02* | (2006.01) |
| *B01D 15/24* | (2006.01) |
| *B01D 15/26* | (2006.01) |
| *B01D 17/02* | (2006.01) |
| *C12N 15/10* | (2006.01) |

(52) U.S. Cl.
CPC .............. *B01D 15/20* (2013.01); *B01D 11/02* (2013.01); *B01D 11/0219* (2013.01); *B01D 15/00* (2013.01); *B01D 15/02* (2013.01); *B01D 15/24* (2013.01); *B01D 15/245* (2013.01); *B01D 15/26* (2013.01); *B01D 17/02* (2013.01); *B01D 17/0202* (2013.01); *C12N 15/1006* (2013.01); *C12N 15/101* (2013.01); *C12N 15/1017* (2013.01)

(58) Field of Classification Search
CPC .............................. B01D 15/20; C12N 15/101
See application file for complete search history.

(56) References Cited

U.S. PATENT DOCUMENTS

| | | | |
|---|---|---|---|
| 5,411,876 A | 5/1995 | Bloch et al. | |
| 6,383,393 B1 | 5/2002 | Colpan et al. | |
| 6,706,858 B2 | 3/2004 | Rothmann et al. | |
| 2003/0065152 A1* | 4/2003 | Rothmann ......... | C12N 15/1017 536/103 |
| 2005/0244882 A1 | 11/2005 | Gauch et al. | |
| 2008/0221372 A1* | 9/2008 | Rothmann .......... | B01L 3/50851 585/1 |
| 2010/0285596 A1* | 11/2010 | Yu ........................ | G01N 1/4055 436/71 |

FOREIGN PATENT DOCUMENTS

| | | |
|---|---|---|
| EP | 0 356 021 A2 | 2/1990 |
| EP | 0 502 589 A2 | 9/1992 |
| EP | 0 509 612 A2 | 10/1992 |
| EP | 0 590 327 A2 | 4/1994 |
| EP | 0 709 466 A2 | 5/1996 |
| EP | 1 256 627 A2 | 11/2002 |
| EP | 2 607 482 A1 | 6/2013 |
| EP | 2 825 646 B1 | 8/2019 |
| WO | 98/59076 A1 | 12/1998 |
| WO | 99/29840 A1 | 6/1999 |
| WO | 03/035867 A1 | 5/2003 |
| WO | 2005/012523 A1 | 2/2005 |
| WO | 2005/070545 A1 | 8/2005 |
| WO | 2008/150826 A1 | 12/2008 |
| WO | 2009/111316 A2 | 9/2009 |
| WO | WO 2010/015835    * | 2/2010 |

(Continued)

OTHER PUBLICATIONS

Supelco Bulletin 910 (Supelco, Guide to Solid Phase Extraction (1998) Sigma Aldrich Co., available at http://www.sigmaaldrich.com/Graphics/Supelco/objects/4600/4538.pdf). (Year: 1998).*
Ishizuka (Designing monolithic double-pore silica for high-speed liquid chromatography, Journal of Chromatography A 1998, 797: 133-137) (Year: 1998).*
Supelco (Guide to Solid Phase Extraction, 1998) (Year: 1998).*
Telepchak et al. (Silica-Based Solid Phase Extraction, downloaded on Jul. 17, 2020 fro URL:< https://link.springer.com/content/pdf/10.1007%2F978-1-59259-292-0_2.pdf) (Year: 2020).*
Wikipedia (downloaded on Feb. 4, 2021 from URL:< https://en.wikipedia.org/wiki/Diammonium_phosphate>) (Year: 2021).*

(Continued)

*Primary Examiner* — Sergio Coffa

(74) *Attorney, Agent, or Firm* — Seed Intellectual Property Law Group LLP

(57) ABSTRACT

A method for obtaining a liquid from a porous solid phase is described. The method comprises forming a liquid seal at a first end of a porous solid phase to which a liquid is bound, wherein liquid of the liquid seal is immiscible with the liquid bound to the solid phase, and applying a pressure differential across the porous solid phase to cause the immiscible liquid to move through the porous solid phase towards a second end of the porous solid phase, thereby displacing the liquid bound to the porous solid phase towards the second end and releasing this liquid from the second end. Recovery of liquid from the solid phase using such methods is increased compared with corresponding methods in which no liquid seal is formed. In preferred embodiments, the liquid used to form the liquid seal is a mineral oil. The methods have particular application in nucleic acid extractions which utilise capture of nucleic acid to a solid phase. Kits and apparatus for performing the methods are also described.

9 Claims, 8 Drawing Sheets

(56) References Cited

FOREIGN PATENT DOCUMENTS

| WO | WO-2010015835 A1 | * | 2/2010 | ......... C12N 15/1003 |
| WO | 2010/108971 A1 | | 9/2010 | |
| WO | 2010/147561 A1 | | 12/2010 | |
| WO | 2011/122841 A2 | | 10/2011 | |
| WO | 2012/007502 A1 | | 1/2012 | |

OTHER PUBLICATIONS

Andrus et al., "Analysis and Purification of Synthetic Nucleic Acids Using HPLC," *Current Protocols in Nucleic Acid Chemistry I*(Supplement 1):10.5.1-10.5.13, 2000.

Eckfeldt et al., "Measurement of Ultrafiltrable Calcium in Serum with Use of the "Worthington Ultrafree Anticonvulsant Drug Filter"," *Clinical Chemistry 26*(13):1871-1873, 1980.

Medvedovici et al., "Retention Phenomena Induced by Large Volume Injection of Solvents Non-Miscible with the Mobile Phase in Reversed-Phase Liquid Chromatography," *Journal of Liquid Chromatography & Related Technologies 30*(2):199-213, 2007.

Supelco Bulletin 910, "Guide to Solid Phase Extraction," Sigma Aldrich Co., URL=http://www.sigmaaldrich.com/Graphics/Supelco/objects/4600/4538.pdf, 1998, 12 pages.

Sur et al., "Immiscible Phase Nucleic Acid Purification Eliminates PCR Inhibitors with a Single Pass of Paramagnetic Particles through a Hydrophobic Liquid," *Journal of Molecular Diagnostics 12*(5):620-628, 2010.

Zymo Research, "8. Columns, Plates, Instruments & Accessories," The Beauty of Science. Catalogue, retrieved from http://www.who-sells-it.com/images/catalogs/4628/22400/ct/the-beauty-of-science-20 . . . on Sep. 24, 2012, p. 147.

"BioRobot 8000 Handbook," Qiagen, Nov. 2002, (1 page).

"BioRobot MDx User Manual," Qiagen, Jul. 2002 (183 pages).

"Guidelines for processing the QIAampR DNA Blood BioRObot® MDx Kit on the epMotion® 5075 VAC workstation," Eppendorf AG, pp. 1-15, 2005 (17 pages).

"QIAamp® DNA Blood BioRobot® MDx Kit Hanbook," Qiagen, pp. 1-39, Apr. 2010 (40 pages).

"QIAampR DNA Blood BioRobotR MDx Kit Handbook," Qiagen, pp. 1-35, Jun. 2004 (36 pages).

"QIAamp® Investigator BioRobot® Kit Handbook," Qiagen, pp. 1-42, Sep. 2008 (44 pages).

"RNeasy® 96 BioRobot® 8000 Handbook," Qiagen, pp. 1-39, Oct. 2006 (40 pages).

"RNeasy ® Micro Handbook," Qiagen, pp. 1-74, Apr. 2003 (76 pages).

Material Safety Data Sheet, "Top Elute Fluid," Qiagen, 2002 (4 pages).

Rompp Lexikon, "Chemie: 10. Auflage," pp. 1141-1142, (4 pages).

Thurman et al., "Comparison of Laboratory Diagnostic Procedures for Detection of *Mycoplasma pneumoniae* in Community Outbreaks," *CID 48*:1244-1249, 2009.

Declaration of Rothmann et al., U.S. Appl. No. 10/586,785, filed Mar. 16, 2007, 8 pages.

Extracts from Online Dictionary, no date provided, 2 pages.

Extract from Qiagen website, "S-Blocks," downloaded Dec. 21, 2018, 1 page.

* cited by examiner

Mineral oil

All trapped liquids are collected when mineral oil was used

Liquid was pushed through the solid phase with oil b)

Hold up of liquid at the interface of the solid phase and the column, and also in the nozzle of column Liquid was pushed through the solid phase without oil a)

Mineral oil prevents liquid from being trapped at interfaces.

Column with buffer buffer

Solid phase

Column with buffer and mineral oil

Mineral oil

Formation of semi-spherical meniscus between mineral oil and buffer

Buffer

Solid phase

Formation of semi-spherical drop (meniscus) at the interface between buffer and mineral oil.

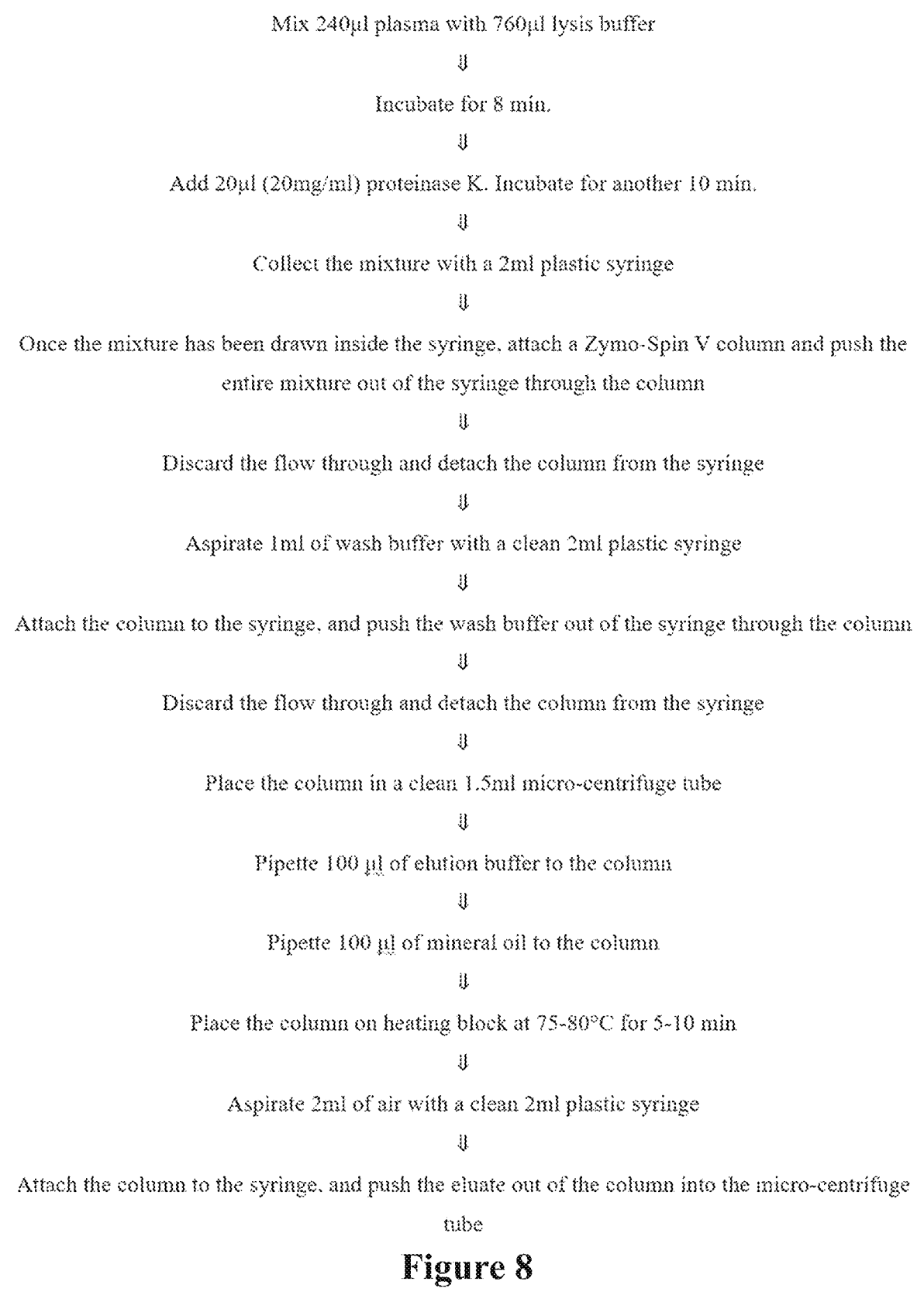

Mix 240µl plasma with 760µl lysis buffer

⇓

Incubate for 8 min.

⇓

Add 20µl (20mg/ml) proteinase K. Incubate for another 10 min.

⇓

Collect the mixture with a 2ml plastic syringe

⇓

Once the mixture has been drawn inside the syringe, attach a Zymo-Spin V column and push the entire mixture out of the syringe through the column

⇓

Discard the flow through and detach the column from the syringe

⇓

Aspirate 1ml of wash buffer with a clean 2ml plastic syringe

⇓

Attach the column to the syringe, and push the wash buffer out of the syringe through the column

⇓

Discard the flow through and detach the column from the syringe

⇓

Place the column in a clean 1.5ml micro-centrifuge tube

⇓

Pipette 100 µl of elution buffer to the column

⇓

Pipette 100 µl of mineral oil to the column

⇓

Place the column on heating block at 75-80°C for 5-10 min

⇓

Aspirate 2ml of air with a clean 2ml plastic syringe

⇓

Attach the column to the syringe, and push the eluate out of the column into the micro-centrifuge tube

Figure 8

METHODS FOR OBTAINING LIQUID FROM A SOLID PHASE

This invention relates to methods for obtaining a liquid from a porous solid phase, and to kits and apparatus for performing the methods.

Methods for isolation of nucleic acids of a quality suitable for downstream applications such as polymerase chain reaction (PCR) and sequencing by adsorption and release from a solid phase are well-established (Vogelstein, B. and Gillespie, D, 1979; PNAS 76, 615). The methods use: (i) a lysis buffer to release nucleic acid from biological samples, (ii) a lysis or a binding buffer to capture nucleic acid to a solid phase, (iii) a wash buffer(s) to wash the captured nucleic acid, and (iv) an elution buffer to release the captured nucleic acid from the solid phase. The quality of nucleic acid isolated using such methods depends on the efficiency of buffer exchange between the lysis, binding, wash and elution steps. Carry-over of lysis, binding or wash buffer into the eluted sample inhibits many downstream applications such as PCR, sequencing and cloning.

In some methods, efficient buffer exchange is accomplished by centrifugation. Centrifugation is an extremely efficient method of removing buffer from the solid phase, and is particularly advantageous for optimum recovery of elution buffer containing released nucleic acid in the elution step.

In other methods, buffer exchange is accomplished by applying a positive pressure at the top of the solid phase, for example by using a syringe or a piston pump to pass air through the solid phase (Zymo-Spin V, Zymo Research), or by applying a negative pressure at the bottom of the solid phase using a vacuum (Fastfilter system, OMEGA Bio-tek). However, formation of a pressure differential across the solid phase to mediate buffer exchange depends on the formation of a good seal. If an air channel is formed through the solid phase before all of the buffer has been removed, the pressure differential is disrupted and residual buffer remains trapped in the solid phase. Residual buffer remaining after the elution step includes nucleic acid, so the yield of nucleic acid obtained from the solid phase is reduced. To obtain high extraction yield, it is necessary to remove the buffer by centrifugation (for example, Zymo-Spin V, Zymo Research & Fastfilter system, OMEGA bio-tek).

The requirement for a centrifugation step to obtain high yield limits the usefulness of pressure differential methods for nucleic acid isolation, and complicates the extraction process. In particular, nucleic acid extraction processes that require a centrifuge cannot be carried out in areas where such equipment is not available, for example in a physician's office or in remote areas. The requirement for a centrifuge is also a particular disadvantage for automated systems because the complexity of such systems is increased. In particular, a robotic arm is required to perform relatively complex actions, such as gripping and movement of sample tubes to transfer them to the centrifuge. This increases the cost and complexity of automated systems, and increases the likelihood of errors occurring.

There is a need, therefore, to provide nucleic acid extraction methods that achieve high yield without requiring a centrifugation step. There is also a need to provide simplified nucleic acid extraction methods that can more readily be automated.

According to the invention, there is provided a method for obtaining a liquid from a porous solid phase, which comprises: forming a liquid seal at a first end of a porous solid phase to which a liquid is bound, wherein liquid of the liquid seal is immiscible with the liquid bound to the solid phase; and applying a pressure differential across the porous solid phase to cause the immiscible liquid to move through the porous solid phase towards a second end of the porous solid phase, thereby displacing the liquid bound to the porous solid phase towards the second end and releasing this liquid from the second end.

The term "porous solid phase" is used herein to mean a solid phase that is permeable to liquid. The permeability may be due to pores or channels in the solid phase material itself or, for example, because the solid phase comprises several particles, such as beads, between which liquid can pass. Examples of porous solid phases include columns that comprise particles, gels, membranes, or beads. Particular examples include any chromatography column in which material bound to the column is to be eluted by passing a liquid through the column. Preferred examples include chromatography columns for liquid chromatography, ion-exchange chromatography, affinity chromatography, reversed-phase chromatography. The solid phase used in chromatography columns is usually a finely ground powder, a gel, or a microporous material. Chromatography columns commonly comprise silica gel, alumina, or cellulose powder. Other examples of porous solid phases suitable for use in methods of the invention include magnetic beads, and devices (such as chips) comprising microfluidic channels.

Typically, the porous solid phase will have affinity for a biomolecule, for example for nucleic acids or proteins. In certain embodiments, the solid phase comprises material to which nucleic acid is able to bind at a lower pH and from which the nucleic acid can be eluted at a higher pH. Several suitable examples of such solid phases are well known to the skilled person. In preferred embodiments, the solid phase comprises an inorganic oxide, preferably silica. In other embodiments, the solid phase comprises ion-exchange material for protein purification. Several suitable examples of such solid phases are known to the skilled person.

Reference herein to liquid "bound" to the porous solid phase means liquid that is associated with the porous solid phase, and which it is desired to release from the porous solid phase.

The term "immiscible liquid" is used herein to refer to the liquid of the liquid seal.

Typically, the liquid bound to the porous solid phase will comprise an aqueous liquid, and the immiscible liquid will comprise a hydrophobic liquid. A property of liquids that are immiscible with each other is that they cannot be diluted in equal parts without separation occurring. It will be appreciated that the immiscible liquid should be substantially immiscible with the liquid bound to the solid phase at least for the period during which the pressure differential is applied across the solid phase.

To form a liquid seal, the immiscible liquid should form a complete layer across the surface of the liquid bound to the porous solid phase at the first end of the porous solid phase.

In certain embodiments, the immiscible liquid is a mineral oil. Suitable mineral oil is molecular biology grade mineral oil. An example is mineral oil that contains only saturated hydrocarbons, for example 36% naphthene (saturated 5- or 6-carbon cyclic paraffins), 64% paraffin. Suitable molecular biology grade mineral oil is available, for example, from Sigma (catalogue no. M5904; density 0.84 g/mL at 25° C.).

It is generally envisaged that the porous solid phase will be arranged such that the pressure differential will cause the immiscible liquid to move down through the porous solid phase. In such arrangements, it is preferred that the immiscible liquid is less dense than the liquid bound to the porous solid phase, so that the immiscible liquid will settle on top of the liquid bound to the porous solid phase. In alternative embodiments, the immiscible liquid may be more dense than the liquid bound to the porous solid phase. However, such liquid should be applied to an upper end of the porous solid phase only when there is no layer of liquid bound to the solid phase above the upper end of the porous solid phase. If necessary, a pressure differential can be applied to move the liquid of any such layer into the porous solid phase before the more dense immiscible liquid is applied. Examples of immiscible liquids that are more dense than aqueous buffer solutions include an organic solvent such as phenol, or a concentrated sucrose solution.

The liquid bound to the porous solid phase may comprise an elution buffer. The content of the elution buffer will depend on the identity of the porous solid phase and on the identity of the material that it is desired to release from the porous solid phase. Examples of typical elution buffers for purification of nucleic acid include Tris-HCl buffer, and Tris-EDTA (TE) buffer. A typical elution buffer for affinity purification of proteins is Glycine-HCl buffer.

It will be appreciated that the liquid bound to the porous solid phase may comprise a biomolecule, such as a protein or nucleic acid, which was bound to the porous solid phase, and which has been released from the porous solid phase into the liquid.

The pressure differential may be applied by increasing the air pressure at the first end of the porous solid phase, for example using a pump or syringe, or by reducing the air pressure at the second end of the porous solid phase, for example by applying a vacuum at the second end of the porous solid phase.

Methods of the invention provide several advantages, as explained below.

The volume of liquid that is obtained from the porous solid phase using methods of the invention is higher than corresponding methods in which no liquid seal is formed. If the liquid contains material, such as a biomolecule, which has been released from the porous sold phase into the liquid, the yield of this material from the solid phase is thereby also increased.

Without being bound by theory, there are believed to be a number of reasons for the increase in the volume of liquid that is obtained from a porous solid phase using methods of the invention.

In conventional methods in which liquid is forced through a column containing a porous solid phase, as the liquid moves down through the column, the upper surface of the liquid approaches the top of the porous solid phase, until only a thin layer of liquid remains above the top of the solid phase. The pressure differential across the solid phase causes disruption of the thin layer of liquid, allowing air to enter the porous solid phase. Air channels are then formed through the porous solid phase, thereby reducing the pressure differential across the solid phase. Residual liquid becomes trapped in the porous solid phase because there is insufficient pressure differential to force this out of the solid phase.

In methods of the invention, the liquid seal is believed to prevent the formation of air channels in the porous solid phase after a pressure differential has been applied, thereby preventing residual liquid from becoming trapped in the solid phase.

For example, in embodiments of the invention in which liquid is forced down through a column containing a porous solid phase, an immiscible liquid may be used which is less dense than the liquid bound to the porous solid phase. In such embodiments, the immiscible liquid forms a layer on top of the liquid bound to the porous solid phase. A pressure differential is applied across the porous solid phase to cause the immiscible liquid, and the liquid bound to the solid phase, to move down through the column. As the upper surface of the liquid bound to the solid phase approaches the top of the solid phase, the layer of immiscible liquid prevents disruption of the liquid below it, and thereby prevents the formation of air channels in the porous solid phase. The pressure differential across the porous solid phase is maintained, thus increasing the amount of liquid that is released from it.

The pores in a porous solid phase used for extraction of nucleic acids typically range from 0.1 to 12 µM. The immiscible liquid enters the pores of the solid phase, and displaces the liquid bound to the porous solid phase from the pores. If the solid phase comprises a porous material contained within a column, liquid can remain trapped at the interface between the solid phase and the column. The liquid seal formed by the immiscible liquid ensures that this trapped liquid is also released from the porous solid phase.

Methods of the invention reduce the variability in the volume of liquid recovered from the porous solid phase, thereby providing consistent recovery and yield from the solid phase. This is an important advantage because results obtained from subsequent processing of different samples collected from the solid phase are more comparable.

When the liquid seal is formed at the first end of the porous solid phase, a semi-spherical meniscus is formed at the interface between the liquid seal and the liquid bound to the solid phase (as shown in FIG. 5). When a pressure differential is applied across the solid phase, the force at the semi-spherical meniscus is directed towards the centre. This is believed to reduce the pressure differential required to displace the liquid bound to the solid phase towards the second end of the solid phase.

The liquid seal also prevents frothing of liquid in the porous solid phase when the pressure differential is applied. Such frothing can inhibit downstream processing of liquid samples collected from the porous solid phase, and reduce the yield of liquid that can be obtained.

The liquid seal prevents evaporation from the first end of the porous solid phase. This allows the solid phase to be heated without a need to cap the solid phase. This is advantageous, particularly for isolation of nucleic acid, because heating of the solid phase is commonly used to increase the amount of nucleic acid that is released from the solid phase. Thus, in some embodiments of the invention, the porous solid phase is heated. Heating can take place before, during, or after formation of the liquid seal at the first end of the porous solid phase, but preferably after formation of the liquid seal.

If the pressure differential is applied for sufficient time that at least some of the immiscible liquid is also released from the porous solid phase, the released immiscible liquid (provided this is less dense than the liquid bound to the solid phase) will form a layer over the top of the liquid in the collected sample. This can be particularly advantageous for subsequent processing of the collected sample. For example, if the liquid seal is a mineral oil, and the liquid in the collected sample contains nucleic acid released from the porous solid phase, the collected sample can be used directly for downstream manipulations in which heating of the sample is required. Examples of such manipulations include nucleic acid amplification reactions (such as polymerase chain reaction, or transcription-mediated amplification), or nucleic acid sequencing reactions.

In conventional methods in which no liquid seal is used when obtaining liquid from a porous solid phase, downstream reactions in which the sample is heated are carried out in capped collection tubes, or a layer of mineral oil is applied before heating the sample, to minimise evaporation. Capped collection tubes, whilst preventing evaporation from the tube, do not prevent evaporation within the tube. The sample volume at the bottom of the tube is reduced, and this can adversely affect the efficiency of the reaction. Addition of a layer of mineral oil before heating maintains the sample volume, but has the potential to contaminate the sample. This can be a serious problem, for example, if the sample is to undergo a nucleic acid amplification reaction.

Methods of the invention in which at least some of the mineral oil is collected with the liquid sample have several advantages. The layer of mineral oil prevents evaporation of the liquid sample, allowing reactions to take place in uncapped collection tubes. The oil layer also prevents changes in the sample volume due to evaporation as the reaction takes place, thereby helping to maintain optimum conditions for the reaction. A further advantage is that the oil layer minimises splashing of the sample liquid, and therefore reduces the chances of cross-contamination between samples.

Methods of the invention allow higher volumes of liquid to be recovered from a porous solid phase than conventional methods, without the need for a centrifugation step. This simplifies methods for obtaining liquid from the solid phase, and allows the methods to be more readily automated.

Methods of the invention may further comprise binding a component to the porous solid phase and releasing the component from the solid phase into the liquid bound to the solid phase prior to forming the liquid seal at the first end of the solid phase. The component may be released from the solid phase by applying an elution buffer to the solid phase prior to forming the liquid seal.

It will be appreciated that methods of the invention may be used with conventional methods for purification in which a biological component, such as a nucleic acid or protein, is bound selectively to a porous solid phase, and then eluted from the porous solid phase. Suitable methods are well-known to the skilled person. Examples of nucleic acid purification methods include methods that use chaotropic agents, such as guanidinium thiocyanate, and organic solvents to lyse cells, and denature proteins (including nucleases, which would otherwise degrade the nucleic acid). For example, Boom et al. (Journal of Clinical Microbiology, 1990, Vol. 28(3): 495-503) describes a method in which a sample containing human serum or urine is contacted with silica particles in the presence of a lysis/binding buffer containing guanidinium thiocyanate. Released nucleic acid binds to the silica particles, which are then washed with a wash buffer containing guanidinium thiocyanate, then with ethanol, and then acetone. The bound nucleic acid is subsequently eluted from the silica particles in an aqueous low salt buffer (Tris-HCl, EDTA, pH 8.0).

Other methods avoid use of chaotropic agents and organic solvents, which are highly inhibitory to enzymatic reactions. Residual amounts of these substances carried over into the eluted sample can interfere with subsequent enzymatic processing of the isolated nucleic acid, for example in nucleic acid sequencing or amplification. Use of chaotropic agents and organic solvents is also undesirable because these reagents are toxic and difficult to handle, and require special provision for their disposal. The requirement for chaotropic salts and organic solvents is avoided in a method described by Hourfar et al. (Clinical Chemistry, 2005, 51(7): 1217-

1222). Plasma sample is mixed with magnetic silica particles in the presence of a lysis/binding buffer containing a kosmotropic salt (ammonium sulphate) before addition of proteinase K. Following separation, the magnetic particles are washed with wash buffer containing proteinase K, and eluted in elution buffer (Tris-HCl, pH 8.5) at 80° C.

Examples of protein purification methods include ion-exchange methods. Methods of the invention may be particularly advantageous for membrane-based ion exchange chromatography. Thermo Scientific Pierce Strong Ion Exchange Spin Columns use membrane-adsorber technology as a chromatographic matrix to fractionate proteins based on their charge differences. According to the manufacturer's protocol, liquid is removed from the column by centrifugation following the application of elution buffer. If instead, a liquid seal is formed according to the invention after the elution buffer has been added to the column, protein purification may be performed using such columns without the need for centrifugation.

According to the invention there is also provided a kit for obtaining a liquid from a porous solid phase, which comprises: a porous solid phase; and a liquid which is immiscible with the liquid to be obtained from the solid phase, and which can form a liquid seal at an end of the porous solid phase.

There is further provided according to the invention a kit for obtaining a liquid from a porous solid phase, which comprises: a porous solid phase; and instructions for applying a liquid, which is immiscible with the liquid to be obtained from the porous solid phase, to an end of the porous solid phase to form a liquid seal at the end of the porous solid phase. The kit may further comprise the immiscible liquid.

There is also provided according to the invention apparatus for obtaining a liquid from a porous solid phase, which comprises: a porous solid phase; a liquid which is immiscible with the liquid to be obtained from the porous solid phase, and which can form a liquid seal at an end of the porous solid phase; and a means for applying a pressure differential across the porous solid phase.

The means for applying a pressure differential across the porous solid phase may comprise a pump, for example a piston pump, a syringe, or a vacuum pump.

The immiscible liquid is preferably less dense than the liquid to be obtained from the porous solid phase. The immiscible liquid may be a hydrophobic liquid, such as a mineral oil.

Preferred embodiments of the invention are now described, by way of example only, with reference to the accompanying drawings in which.

Figure 5:
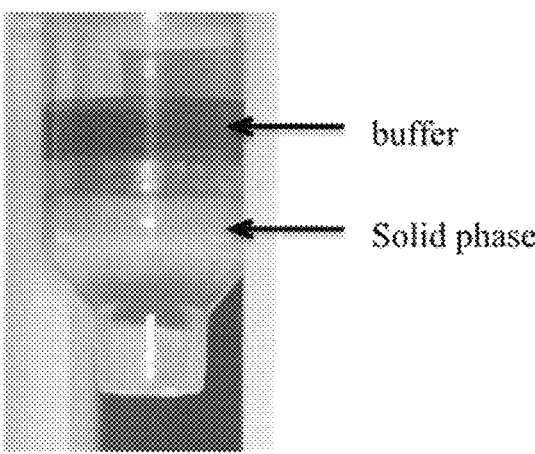
Figure 5:
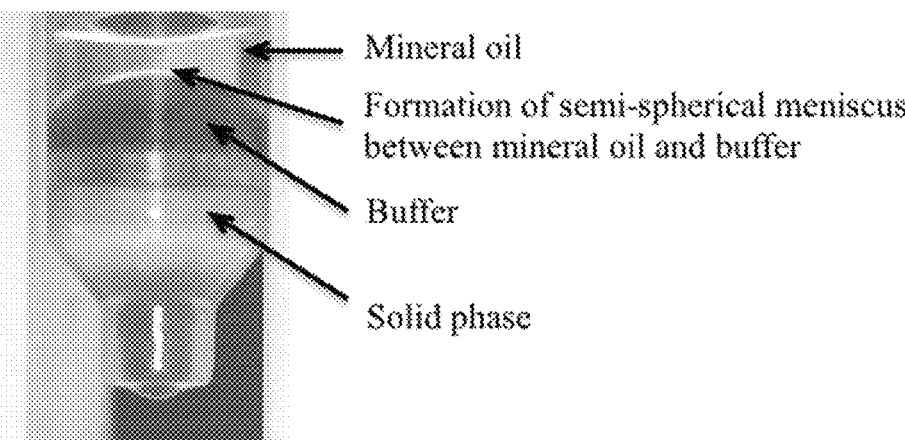
Figure 6:
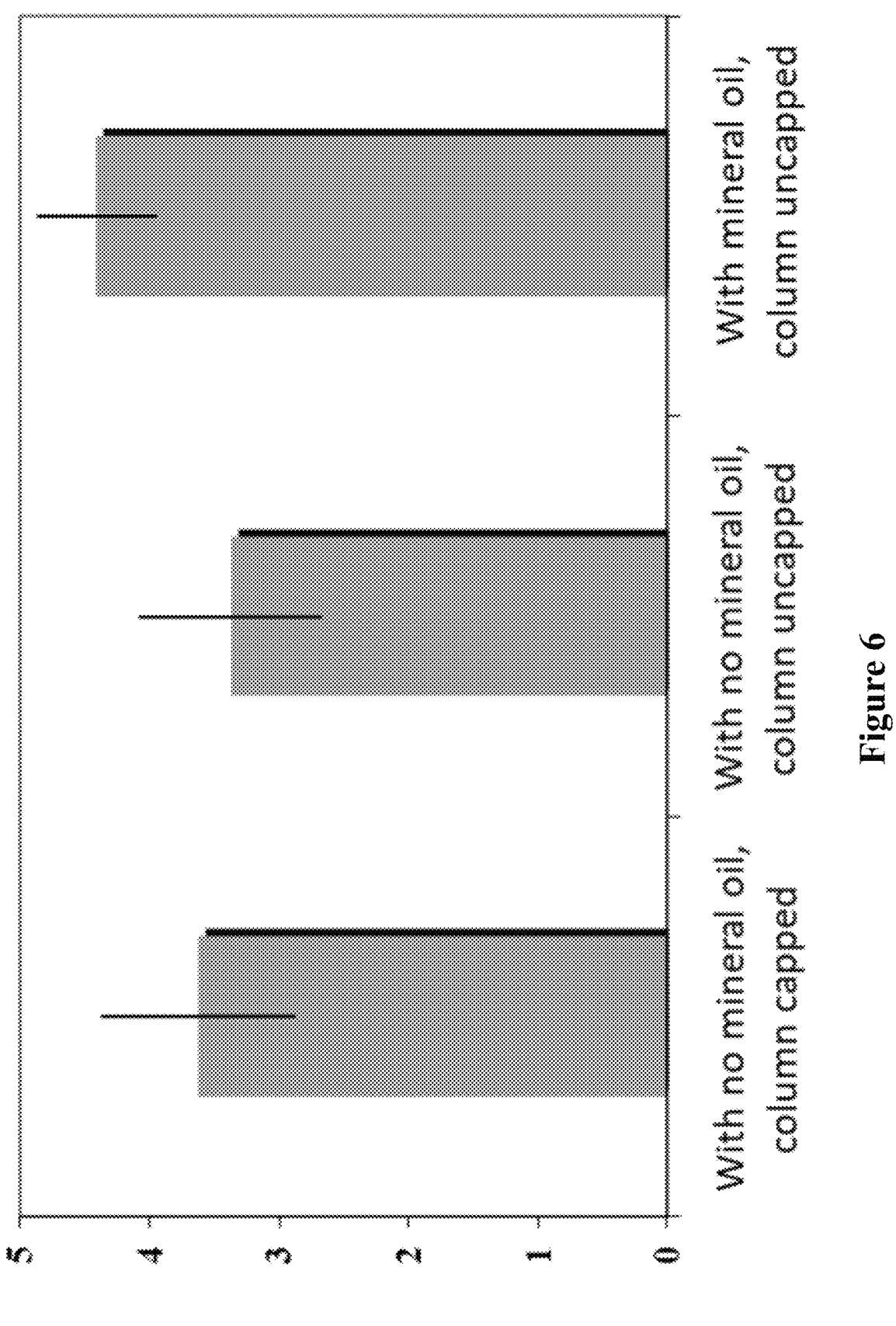
Figure 7:
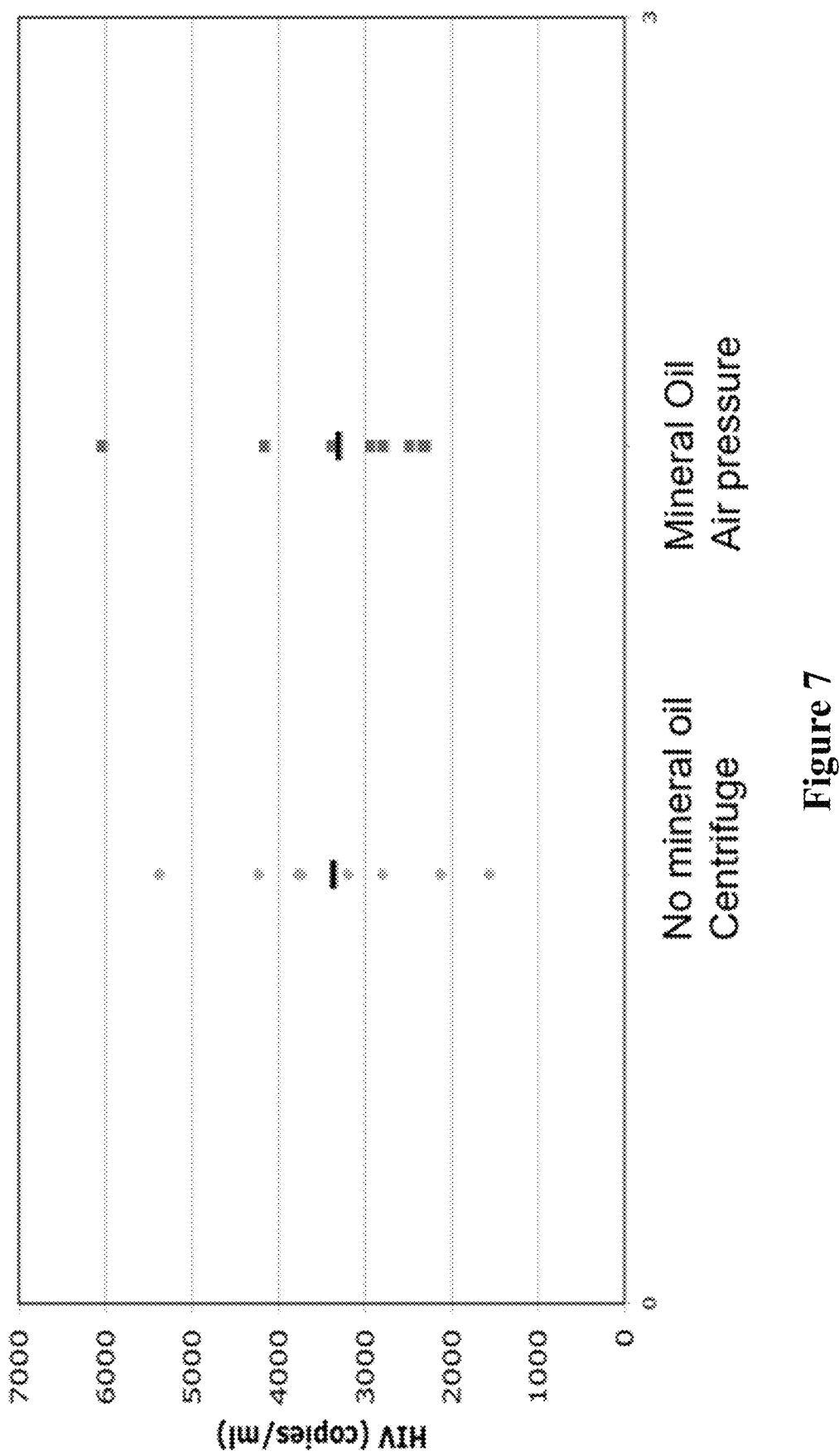

FIG. 5 shows photographs of the lower end of columns containing a silica-based solid phase with a buffer containing a red coloured dye bound to the solid phase. In figure (a) there is no layer of mineral oil over the buffer bound to the solid phase. In figure (b) there is a layer of mineral over the buffer bound to the solid phase. A semi-spherical meniscus can be seen at the interface between the mineral oil and the buffer;

FIG. 6 shows a comparison of the results from detection of amplified HIV-1 RNA eluted from porous solid phases in a capped column with no mineral oil, an uncapped column with no mineral oil, and an uncapped column with a layer of mineral oil over the solid phase; and FIG. 7 shows the yield of nucleic acid eluted from a porous solid phase using a method of the invention compared with a conventional method in which liquid bound to the column was removed by centrifugation. The black horizontal bars show the average yield in each case.

FIG. 8 shows a flowchart corresponding to the procedure of Example 5.

EXAMPLE 1

Use of Mineral Oil Increases the Recovery of Liquid from a Solid Phase

Figure 1:
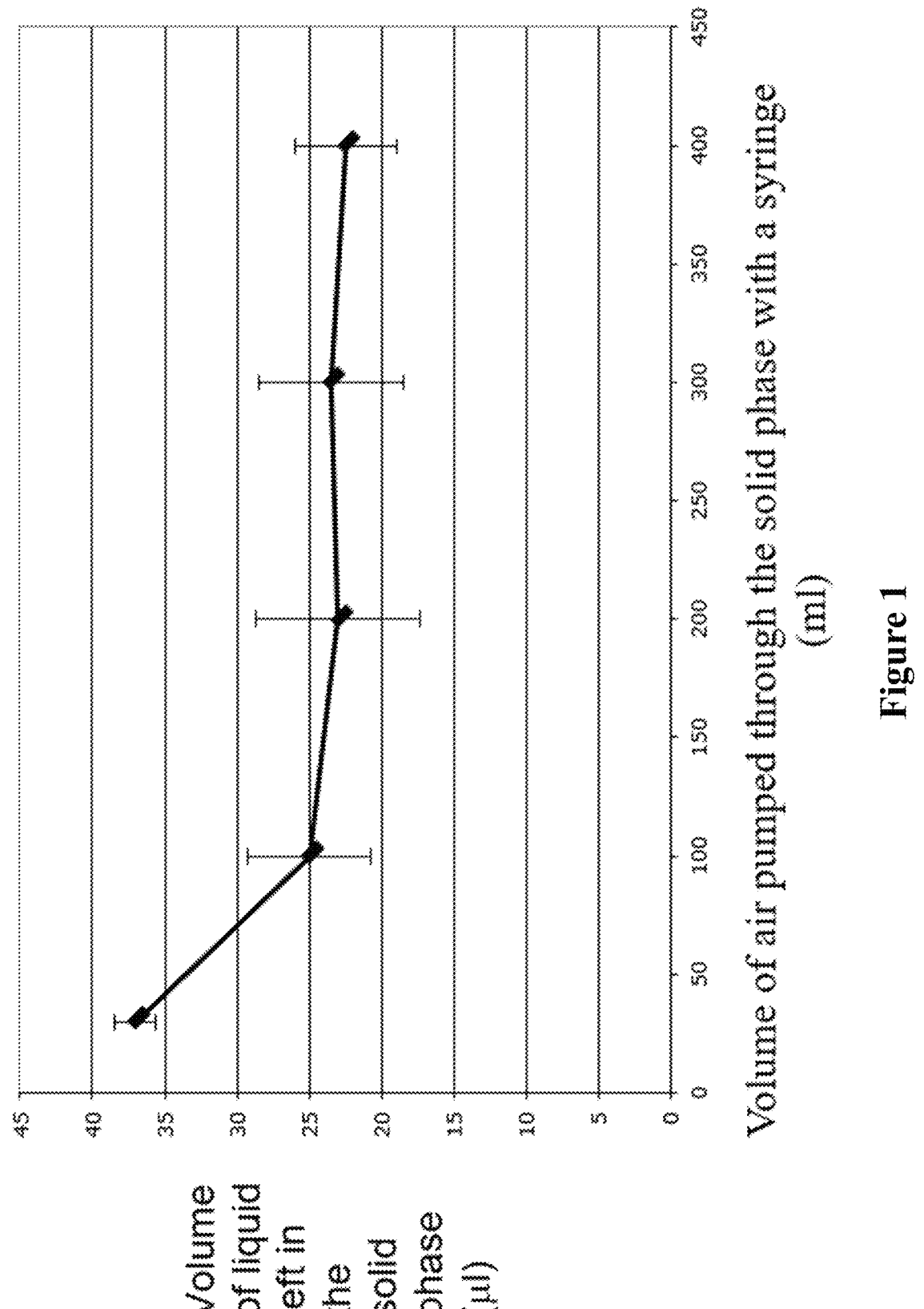
FIG. 1 shows the volume of liquid remaining in a porous solid phase after different volumes of air were pumped through the solid phase using a syringe in the absence of a liquid seal.

A silica-based solid phase was loaded with 0.5 ml lysis buffer (0.2M sodium citrate buffer pH 4.3, 0.3 M ammonium sulphate, 0.4% Triton-X 100), and then 30 ml, 100 ml, 200 ml, 300 ml, or 400 ml of air was passed through it using a syringe. The volume of liquid left in the solid phase is recorded in FIG. 1. The data shows that there is always a volume of residual buffer retained in the solid phase, even after 400 ml of air has been pumped through it.

Figure 2:
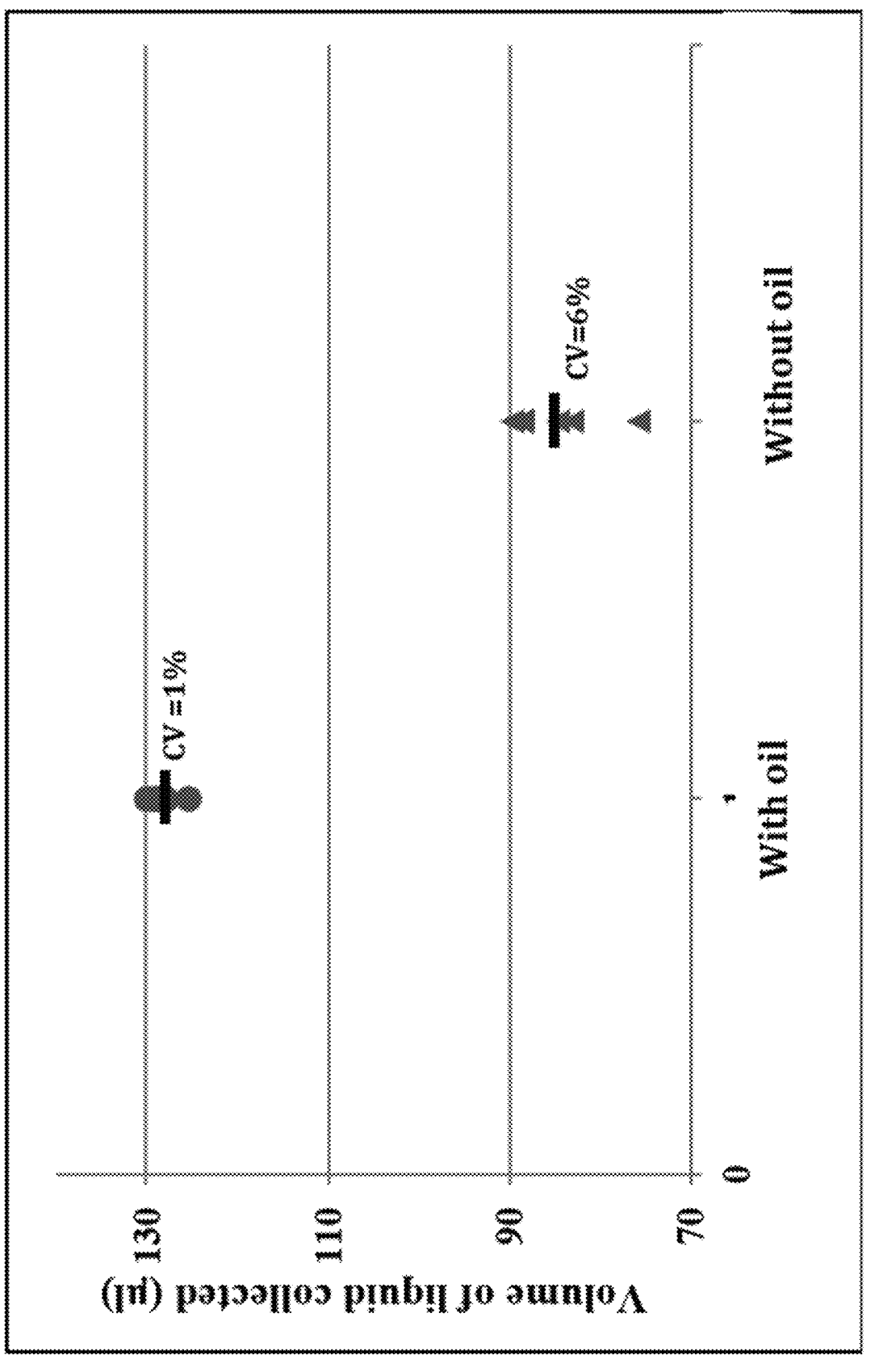
FIG. 2 shows the volume of liquid collected from a porous solid phase by pumping air through the solid phase with and without a liquid seal (a layer of mineral oil) at an upper end of the porous solid phase.

The recovery of liquid from the solid phase was increased by use of mineral oil according to the invention. A silica-based solid phase was loaded with 150 µl elution buffer (10 mM Tris-HCl pH 8.5). Mineral oil was then applied to form a liquid seal at the upper end of the solid phase, prior to pumping air through the solid phase with a syringe. The volume of liquid collected from the solid phase was recorded, and compared with the volume of liquid collected without application of mineral oil. The results are shown in FIG. 2. The data points represent six individual measurements of liquid collected with and without mineral oil. The black bar indicates the average volume collected, and "CV" is the coefficient of variation. The results show that mineral oil increases the recovery of liquid from the solid phase and reduces the variation in the amount of liquid recovered.

EXAMPLE 2

Use of Mineral Oil Increases the Yield of Nucleic Acid from a Solid Phase

Figure 3:
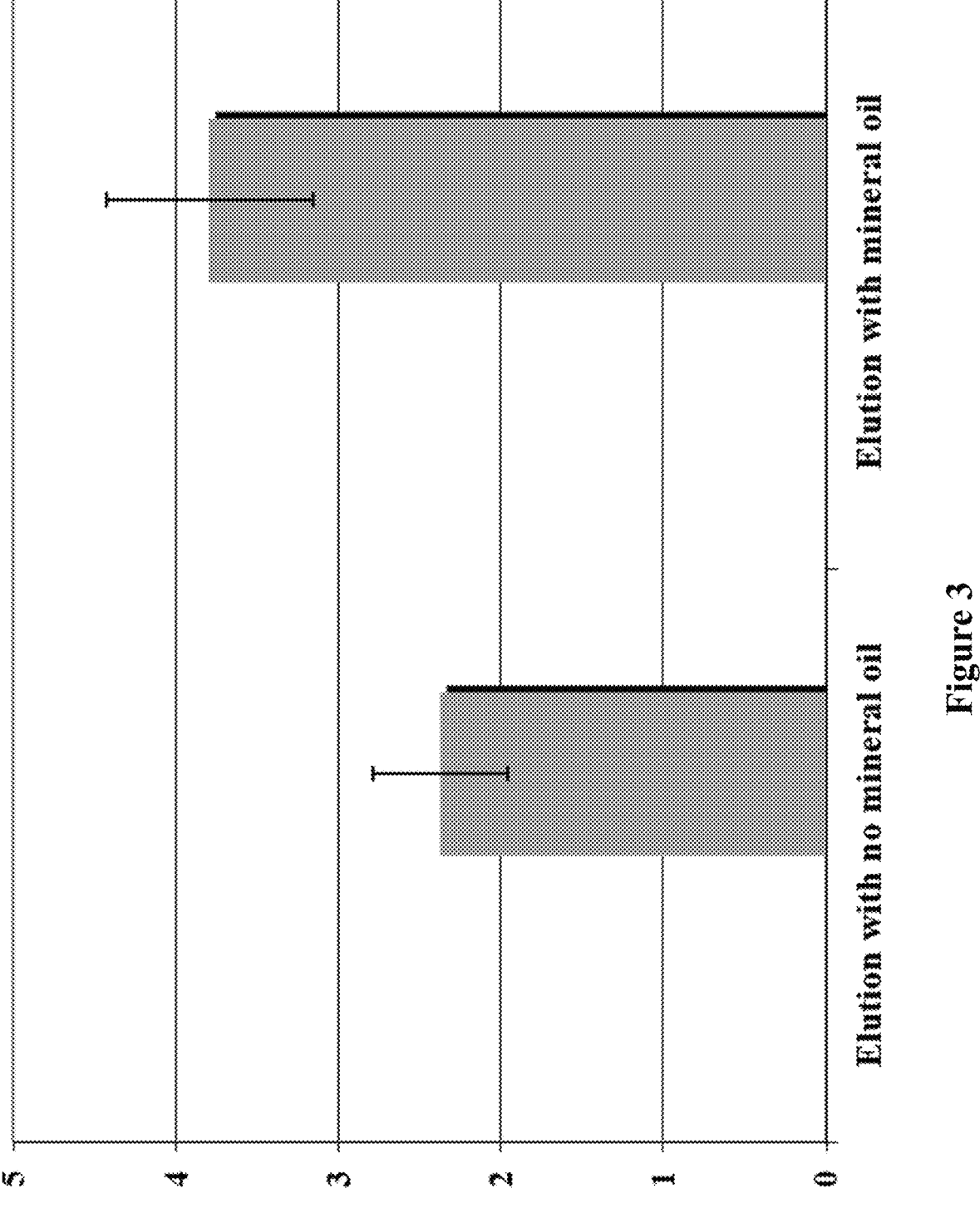
FIG. 3 shows the strength of the assay signal obtained following amplification and detection of HIV-1 RNA eluted from a porous solid phase with and without a liquid seal (a layer of mineral oil) at an upper end of the porous solid phase.

RNA was extracted from human plasma spiked with HIV-1 RNA using a silica-based solid phase in a column. RNA was eluted from the solid phase with and without a liquid seal formed by a layer of mineral oil at the upper end of the solid phase. HIV-1 RNA in the eluate was amplified, and specifically detected by dipstick assay using a method as described in Dineva et al (Journal of Clinical Microbiology, 2005, Vol. 43(8): 4015-4021). The assay signals were scored from 0.5 to 5 using a scorecard, with 5 being strongest and 0.5 weakest. The results, shown in FIG. 3, demonstrate that the assay signal was increased by over 50% when mineral oil was used. It is concluded that the yield of nucleic acid from the solid phase is increased by use of mineral oil.

EXAMPLE 3

Use of Mineral Oil to Obtain Liquid Trapped at Interfaces

Figure 4:
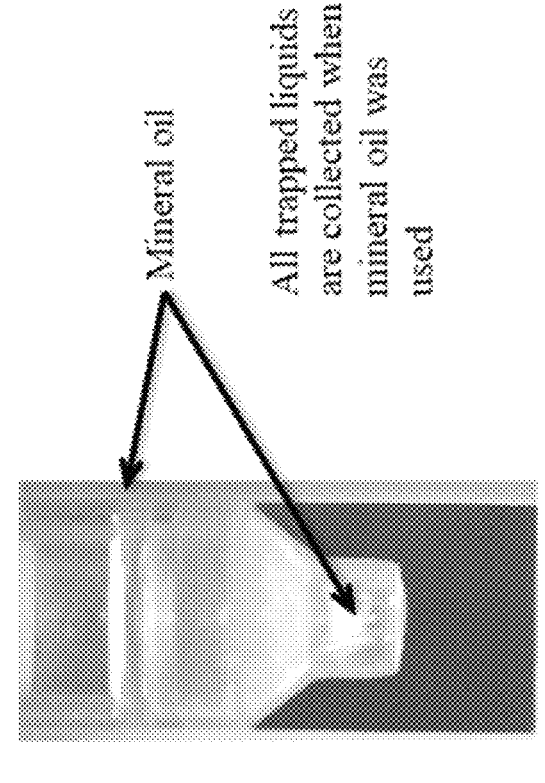
FIG. 4 shows photographs of the lower end of columns containing a silica-based solid phase through which liquid containing a red coloured dye has been passed (a) without, and (b) with a liquid seal (a layer of mineral oil) at an upper end of the solid phase.
Figure 4:
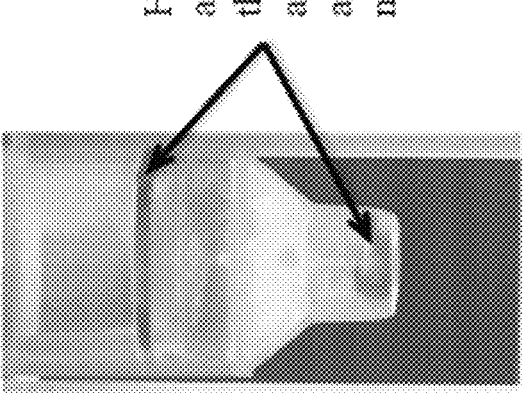

Liquid containing a red coloured dye was applied to a column containing a porous solid phase, and then removed from the solid phase by pumping air through the column using a syringe. The liquid leaves the column through an nozzle at the lower end of the column. A photograph of the lower end of the column with the nozzle is shown in FIG. 4(*a*). Liquid remains trapped in at an interface between the solid phase and the column, and in the nozzle. FIG. 4(*b*) shows the effect of applying a layer of mineral oil over the solid phase before air is pumped through the column. No liquid is trapped at the interface of the solid phase with the column, or in the nozzle.

It is concluded that use of mineral oil also increases the amount of liquid that can be obtained from the solid phase by removing liquid from the interface of the solid phase with the solid phase support.

EXAMPLE 4

Formation of a Semi-Spherical Meniscus at the Interface Between Mineral Oil and Aqueous Liquid Bound to the Solid Phase FIG. 5 shows that when mineral oil is layered at an upper end of a porous solid phase to which an aqueous liquid is bound, a semi-spherical meniscus is formed at the interface between the mineral oil and the aqueous liquid. When a pressure differential is applied across the solid phase, the force at the semi-spherical meniscus is directed towards the centre. It is believed that this reduces the pressure differential required to displace the liquid bound to the solid phase towards the second end of the solid phase.

EXAMPLE 5

A procedure for isolation of nucleic acid from a plasma sample using a method of the invention In this example, a detailed procedure for isolation of nucleic acid from a plasma sample using a method of the invention is described.

A plasma sample is lysed, digested with a proteinase, and then applied to a porous solid phase contained within a column. Nucleic acid in the lysed plasma sample binds to the solid phase, and is then washed with a wash buffer. Next, elution buffer is applied to the column to release the nucleic acid from the solid phase. Elution buffer containing the released nucleic acid is then obtained from the solid phase using a method of the invention.

Buffers:

Lysis buffer: comprises a kosmotropic salt, and a non-ionic detergent at acidic pH;

Wash buffer: comprises Tris-HCl at acidic pH;

Elution buffer: comprises Tris-HCl at alkaline pH.

EXAMPLE 6

Nucleic Acid Yield Using a Method of the Invention is Improved in Uncapped Columns In this example, RNA was extracted from human plasma spiked with HIV-1 RNA by carrying out the procedure described in Example 5 using an uncapped column. For comparison, extractions were also performed with: (i) a capped column; or (ii) an uncapped column; without adding mineral oil after the addition of elution buffer.

HIV-1 RNA in the eluate was amplified, and specifically detected by dipstick assay using a method as described in Dineva et al (Journal of Clinical Microbiology, 2005, Vol. 43(8): 4015-4021). The assay signals were scored from 0.5 to 5 using a scorecard, with 5 being strongest and 0.5 weakest. The results, shown in FIG. 6, demonstrate that the best dipstick signal was obtained when mineral oil was used, indicating that the yield of RNA was greatest from the uncapped column with mineral oil.

EXAMPLE 7

Nucleic Acid Yield Using a Method of the Invention is Comparable with a Centrifugation Method Plasma was spiked with HIV-1 at 5000 copies/ml. RNA was extracted from the plasma and bound to a porous solid phase in two separate columns. Elution buffer was added to each column, followed by addition of a layer of mineral oil to form a liquid seal at the upper end of the solid phase of one of the columns. RNA was then eluted from the solid phase with the mineral oil by applying air pressure to the top of the solid phase. RNA was eluted from the other column by centrifugation. HIV-1 RNA in the eluted samples was quantified by reverse transcription-polymerase chain reaction (RT-PCR). The results are shown in FIG. 7. The black horizontal bars indicate average extraction yield. It is concluded that the yield of RNA using a method of the invention was comparable with the centrifugation method.

The invention claimed is:

1. An apparatus for obtaining a releasably bound liquid from a porous solid phase, the apparatus comprising:
   a porous solid phase to which a liquid can be releasably bound, wherein the porous solid phase comprises silica;
   an immiscible liquid that is immiscible with the liquid that can be releasably bound to the porous solid phase, wherein:
     the immiscible liquid is less dense than the liquid that can be releasably bound to the porous solid phase,
     the immiscible liquid is capable of forming a liquid seal at a first end of the porous solid phase,
     the liquid seal comprises a layer of the immiscible liquid, and the immiscible liquid comprises a mineral oil; and
   a means for applying a pressure differential across the porous solid phase by increasing air pressure at the first end of the porous solid phase,
   wherein:
   in use, the liquid seal forms a complete layer of the immiscible liquid across a surface of the liquid releasably bound to the porous solid phase, forming a semispherical meniscus at an interface between the liquid seal and the liquid releasably bound to the porous solid phase;
   the complete layer of the immiscible liquid prevents disruption of the liquid releasably bound to the porous solid phase when the air pressure is increased at the first end of the solid phase by the means for applying the pressure differential across the porous solid phase, such that the layer of the immiscible liquid moves through the porous solid phase towards a second end of the porous solid phase and displaces the releasably bound liquid towards the second end until the releasably bound liquid is released from the second end;
   the apparatus is capable of obtaining the releasably bound liquid from the porous solid phase without centrifugation; and
   the apparatus does not comprise a centrifuge.

2. The apparatus of claim 1, wherein the means for applying a pressure differential across the porous solid phase by increasing air pressure at the first end of the porous solid phase comprises a pump or a syringe.

3. The apparatus of claim 1, wherein the means for applying a pressure differential across the porous solid phase by increasing air pressure at the first end of the porous solid phase is capable of causing the layer of immiscible liquid to move through the solid phase.

4. The apparatus of claim 1, wherein the porous solid phase has affinity for a nucleic acid or a protein.

5. The apparatus of claim 1, wherein (i) the porous solid phase has affinity for the nucleic acid in a binding buffer having an acidic pH, and (ii) the nucleic acid can be eluted from the porous solid phase by an elution buffer having an alkaline pH.

6. An apparatus according to claim 1, wherein in use the volume of the immiscible liquid is equal to the volume of the liquid releasably bound to the porous solid phase.

7. An apparatus for obtaining a releasably bound liquid from a porous solid phase, the apparatus comprising:
   a porous solid phase to which a liquid can be releasably bound, wherein the porous solid phase comprises silica;
   an immiscible liquid that is immiscible with the liquid that can be releasably bound to the porous solid phase, wherein:
     the immiscible liquid is less dense than the liquid that can be releasably bound to the porous solid phase,
     the immiscible liquid is capable of forming a liquid seal at a first end of the porous solid phase,
     the liquid seal comprises a layer of the immiscible liquid,
     the immiscible liquid comprises a mineral oil; and
   a means for applying a pressure differential across the porous solid phase by increasing air pressure at the first end of the porous solid phase,
   wherein:
   the apparatus is capable of obtaining the releasably bound liquid from the porous solid phase without centrifugation; and
   the apparatus does not comprise a centrifuge.

8. An apparatus according to claim 7, wherein the volume of the immiscible liquid is equal to the volume of the liquid releasably bound to the porous solid phase.

9. An apparatus for obtaining a releasably bound liquid from a porous solid phase, the apparatus comprising:
   a porous solid phase to which a liquid can be releasably bound, wherein the porous solid phase comprises silica;
   an immiscible liquid that is immiscible with the liquid that can be releasably bound to the porous solid phase, wherein:
     the immiscible liquid is less dense than the liquid that can be releasably bound to the porous solid phase,
     the immiscible liquid is capable of forming a liquid seal at a first end of the porous solid phase,
     the liquid seal comprises a layer of the immiscible liquid, and the immiscible liquid comprises a mineral oil; and
   a means for applying a pressure differential across the porous solid phase by increasing air pressure at the first end of the porous solid phase,
   wherein:
   in use, a volume of the immiscible liquid is such that the liquid seal forms a complete layer of the immiscible liquid across a surface of the liquid releasably bound to the porous solid phase, forming a semi-spherical meniscus at an interface between the liquid seal and the liquid releasably bound to the porous solid phase;
   the complete layer of the immiscible liquid prevents disruption of the liquid releasably bound to the porous solid phase when the air pressure is increased at the first end of the solid phase by the means for applying the pressure differential across the porous solid phase, such that the layer of the immiscible liquid moves through the porous solid phase towards a second end of the porous solid phase and displaces the releasably bound liquid towards the second end until the releasably bound liquid is released from the second end;

the apparatus is capable of obtaining the releasably bound liquid from the porous solid phase without centrifugation; and the apparatus does not comprise a centrifuge.

* * * * *